United States Patent
Wu (10) Patent No.: US 11,903,822 B2
(45) Date of Patent: Feb. 20, 2024

(54) PUSH MECHANISM FOR INTERFACING A DRIVE MECHANISM HANDPIECE WITH AN INTROACULAR LENS CARTRIDGE

(71) Applicant: Alcon Inc., Fribourg (CH)

(72) Inventor: Yinghui Wu, Cedar Hill, TX (US)

(73) Assignee: Alcon Inc., Fribourg (CH)

( * ) Notice: Subject to any disclaimer, the term of this patent is extended or adjusted under 35 U.S.C. 154(b) by 792 days.

(21) Appl. No.: 16/999,415

(22) Filed: Aug. 21, 2020

(65) Prior Publication Data

US 2021/0052369 A1 Feb. 25, 2021

(51) Int. Cl.
*A61F 2/16* (2006.01)

(52) U.S. Cl.
CPC .......... *A61F 2/167* (2013.01); *A61F 2/1678* (2013.01); *A61F 2002/1683* (2013.01)

(58) Field of Classification Search
CPC ....... A61M 39/00; A61F 2/167; A61F 2/1678; A61F 2002/1683; A61F 2/1664; A61F 2/1672

See application file for complete search history.

(56) References Cited

U.S. PATENT DOCUMENTS

| | | | |
|---|---|---|---|
| 5,388,589 A * | 2/1995 | Davis | A61B 10/0275 606/167 |
| 5,616,148 A * | 4/1997 | Eagles | A61F 2/167 606/107 |
| 8,647,382 B2 | 2/2014 | Kudo | |
| 9,314,373 B2 | 4/2016 | Kudo | |
| 9,421,092 B2 | 8/2016 | Brown | |
| 2004/0059343 A1* | 3/2004 | Shearer | A61F 2/1664 606/107 |
| 2005/0149057 A1* | 7/2005 | Rathert | A61F 2/167 606/107 |
| 2010/0094309 A1 | 4/2010 | Boukhny | |
| 2019/0224002 A1 | 7/2019 | Springer | |

* cited by examiner

*Primary Examiner* — Ashley L Fishback
*Assistant Examiner* — Chima U Igboko
(74) *Attorney, Agent, or Firm* — Patterson + Sheridan, LLP (57) ABSTRACT

Systems, methods, and apparatuses for inserting an intraocular lens (IOL) into an eye, are provided. The apparatus comprises an IOL cartridge comprising a nozzle, a compartment, a plunger, and a plunger case. The nozzle is in fluid communication with the compartment, and the plunger case is in fluid communication with the compartment. The plunger is disposed within the plunger case. The plunger case includes flexible members extending from an outer surface of the plunger case. The IOL cartridge is configured to removably attach to a handpiece.

12 Claims, 6 Drawing Sheets

PUSH MECHANISM FOR INTERFACING A DRIVE MECHANISM HANDPIECE WITH AN INTROACULAR LENS CARTRIDGE

TECHNICAL FIELD

The present disclosure generally relates to eye surgery and, more particularly, some embodiments may generally relate to systems, methods, and apparatuses for removably attaching a drive mechanism handpiece to an intraocular lens (IOL) cartridge.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery.

For cataract surgery, a surgical procedure may require incisions and insertion of tools within an eye to replace the clouded lens with an IOL. An insertion tool can be used for delivery of the IOL into the eye. By way of example, the insertion tool may include a plunger for forcing the IOL out of the nozzle of the insertion tool. In some instances, the IOL may be preloaded in the insertion tool. In other instances, a separate bay may be loaded into the insertion tool. The plunger may engage the IOL to advance the IOL from the bay, through a nozzle, and into the eye.

SUMMARY

In an exemplary embodiment, the present disclosure provides an apparatus for delivery of an intraocular lens (IOL) into an eye. The apparatus may include an IOL cartridge comprising a nozzle, a compartment, a plunger, and a plunger case. The compartment may be configured to receive the IOL. The nozzle may be in fluid communication with the compartment, and the plunger case may be in fluid communication with the compartment. The plunger may be disposed within the plunger case. The plunger case may include flexible members extending from an outer surface of the plunger case. The IOL cartridge may be configured to removably attach to a handpiece.

In another exemplary embodiment, the present disclosure provides an apparatus for delivery of an IOL into an eye. The apparatus may include a handpiece comprising a housing and a push rod disposed within the housing. The housing may include flexible clips. A distal end of the push rod may be configured to removably attach to an IOL cartridge.

In another exemplary embodiment, the present disclosure provides a method for delivery of an IOL into an eye. The method may comprise inserting a plunger case of an IOL cartridge into a housing of a handpiece. The plunger case may include flexible members extending from an outer surface of the plunger case. The IOL cartridge may further comprise a nozzle, a plunger, a case, and a compartment comprising the IOL. The compartment may further comprise the IOL and an IOL folding mechanism. The nozzle may be in fluid communication with the compartment. The plunger case may be in fluid communication with the compartment. The plunger may be disposed within the plunger case. The method may further include receiving a distal end of a push rod of the handpiece between flexible prongs of the plunger and further inserting the plunger case within the housing of the handpiece, causing internal features of the housing to move the flexible prongs inward to release the plunger from a locked position and to secure the distal end of the push rod between the flexible prongs. The method may further comprise receiving portions of the flexible members within apertures of the housing of the handpiece to lock the IOL cartridge to the handpiece.

In another exemplary embodiment, the present disclosure provides an apparatus for delivering an IOL. The apparatus may comprise an IOL cartridge comprising a compartment for receiving an IOL, a plunger case having a distal end coupled to the compartment and a proximal end, and a plunger disposed within the plunger case. The plunger case may include flexible members extending from an outer surface of the plunger case. The apparatus may further comprise a handpiece configured to be removably coupled to the plunger case and comprising a housing and a push rod disposed within the housing and configured to releasably couple to the plunger of the plunger case.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments of the present disclosure provide a variety of preloaded IOL cartridge designs. These preloaded cartridges may be used with handpieces that include different types of drive mechanisms. Particular embodiments of the present disclosure allow interchangeability between different handpieces such as disposable and reusable handpieces, and various preloaded IOL cartridge designs. The disposable handpieces may include non-powered drive mechanisms that are not electrically powered. The reusable handpieces may include non-powered drive mechanisms (e.g., simply manual pushing or screwing; manually actuated via a fluid or a resilient member such as a spring) as well as electrically powered drive mechanisms (e.g., stator windings). It should be noted that these types of handpieces are examples and that other types of handpieces or drive mechanisms may be utilized in accordance with particular embodiments of the present disclosure.

Particular embodiments of the present disclosure include a standard interface mechanism that employs a push only functionality for assembling the handpiece with the preloaded IOL cartridge, delivering the IOL, and disengaging the handpiece from the used cartridge if needed. The standard interface allows the different types of handpieces to be easily paired to and utilized with the preloaded IOL cartridges for IOL implantation. After IOL implantation, the preloaded IOL cartridges can be easily detached from the reusable handpieces.

The handpiece may be secured to the preloaded IOL cartridge by sliding an end of the handpiece over the plunger case of the IOL cartridge. In certain embodiments, the plunger case may have a flexible member that engages with a clip on the handpiece to secure the handpiece around the plunger case.

Additionally, an internal feature of the handpiece may engage with and press inward a resilient prong of a tail spring of the plunger that is disposed within the plunger case of the IOL cartridge. The resilient prong may be pressed inward to release the plunger from its initial locked position within the plunger case. The plunger may be locked to prevent movement during shipping or storing. When the prong of the plunger tail spring is compressed, the prong may engage with the push rod of the handpiece. Once engaged, the push rod and the plunger are ready for advancement to deliver the IOL that is contained within the IOL cartridge. Once the IOL delivery has been completed, the handpiece may be disconnected from the used IOL cartridge by pressing inward the clip on the handpiece and sliding the IOL cartridge out from within the handpiece.

Figure 1:
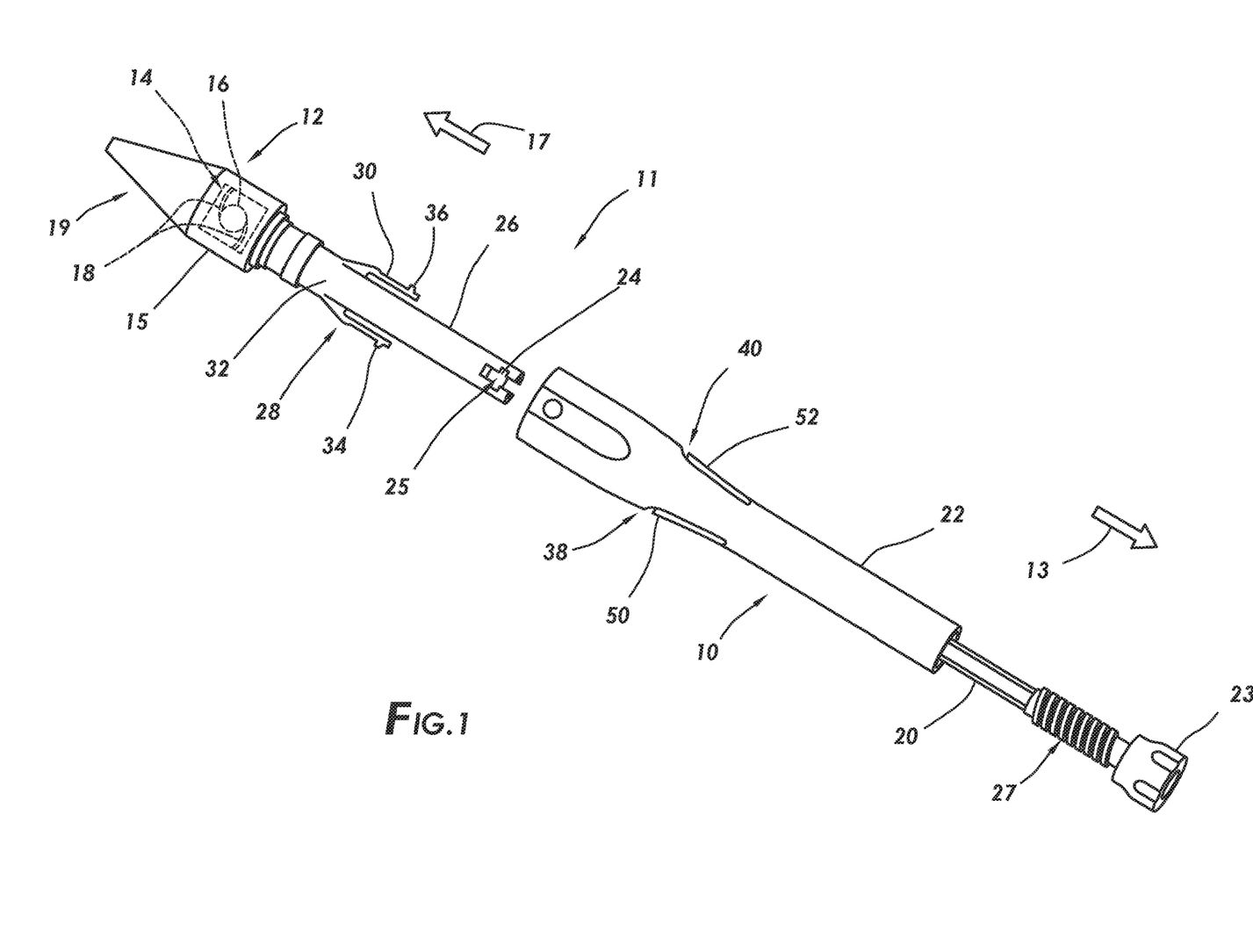
FIG. 1 illustrates a top perspective view of an IOL cartridge and a handpiece, in accordance with some embodiments of the present disclosure.

FIG. 1 illustrates a partially exploded view of an IOL insertion tool 11, which may be formed by assembling a handpiece 10 and an IOL cartridge 12, in accordance with particular embodiments of the present disclosure. The handpiece 10 and the IOL cartridge 12 may be removably attached to one another. In operation, the handpiece 10 may be actuated to advance an IOL 14 from the IOL cartridge 12.

The IOL cartridge 12 may include a compartment 15 containing the IOL 14. The IOL 14 may include a lens 16 and haptic extensions 18. The haptic extensions 18 may be side struts (or other suitable extensions) extending from the lens 16 that may stabilize the IOL 14 when it may be disposed within the patient's eye. It should be understood that the IOL 14 is merely exemplary and that techniques disclosed herein may be used with any suitable IOL. For example, a modular IOL (not shown) that includes a lens portion disposable in a base with haptic extensions may also be used.

The IOL cartridge 12 may also include a nozzle 19 that is in fluid communication with the compartment 15. The IOL cartridge 12 may include a folding mechanism (not shown) to fold the IOL 14. For example, the IOL cartridge 12 may include calipers or arms (not shown) to fold the IOL 14 for delivery into an eye. A plunger 24 may be movably disposed within a plunger case 26 of the IOL cartridge 12. In the illustrated embodiment, only a tail 25 of the plunger 24 is visible, the tail 25 extending from the plunger case 26. The plunger case 26 may be a hollow and rigid member that removably attaches to the handpiece 10. The plunger case 26 may include flexible members 28 and 30 that extend from an outer surface 32 of the plunger case 26. Tabs 34 and 36 may extend outward from the flexible members 28 and 30.

The handpiece 10 may be a rigid member of a tubular shape and may be utilized in conjunction with the IOL cartridge 12 to deliver the IOL 14 into an eye. The handpiece 10 may comprise a variety of materials, for example, plastic and/or metal. It should be noted that various handpieces may be used with different types of IOL cartridges. The handpiece 10 may include an electrically powered or a non-electrically powered drive mechanism that may include a push rod 20 movably disposed within a housing 22 of the handpiece 10. The push rod 20 may be manually actuated via a rotatable dial 23, which may cooperate with a fluid or a resilient member such as a spring 27 or another actuation mechanism. The push rod 20 may be removably coupled to the plunger 24 that is movably disposed within the plunger case 26 of the IOL cartridge 12.

The housing 22 of the handpiece 10 may include slots 38 and 40. The slots 38 and 40 may be adjacent to flexible clips 50 and 52. The clips 50 and 52 may extend from opposing sides of the handpiece 10. For assembly, the plunger case 26 may be inserted into the housing 22 of the handpiece 10 such that the tabs 34 and 36 extend into the slots 38 and 40, to removably couple the IOL cartridge 12 to the handpiece 10 to form an insertion tool. In general, for the purposes of discussing and describing the various components and features of the handpiece 10 and the IOL cartridge 12 of the IOL insertion tool 11, reference to a proximal end or direction may refer to a direction more towards an end of the handpiece 10 comprising the rotatable dial 23, according to directional arrow 13. Likewise, reference to a distal end or direction may refer to a direction more towards an end of the IOL cartridge 12 comprising the nozzle 19, according to directional arrow 17.

Figures 2, 3:
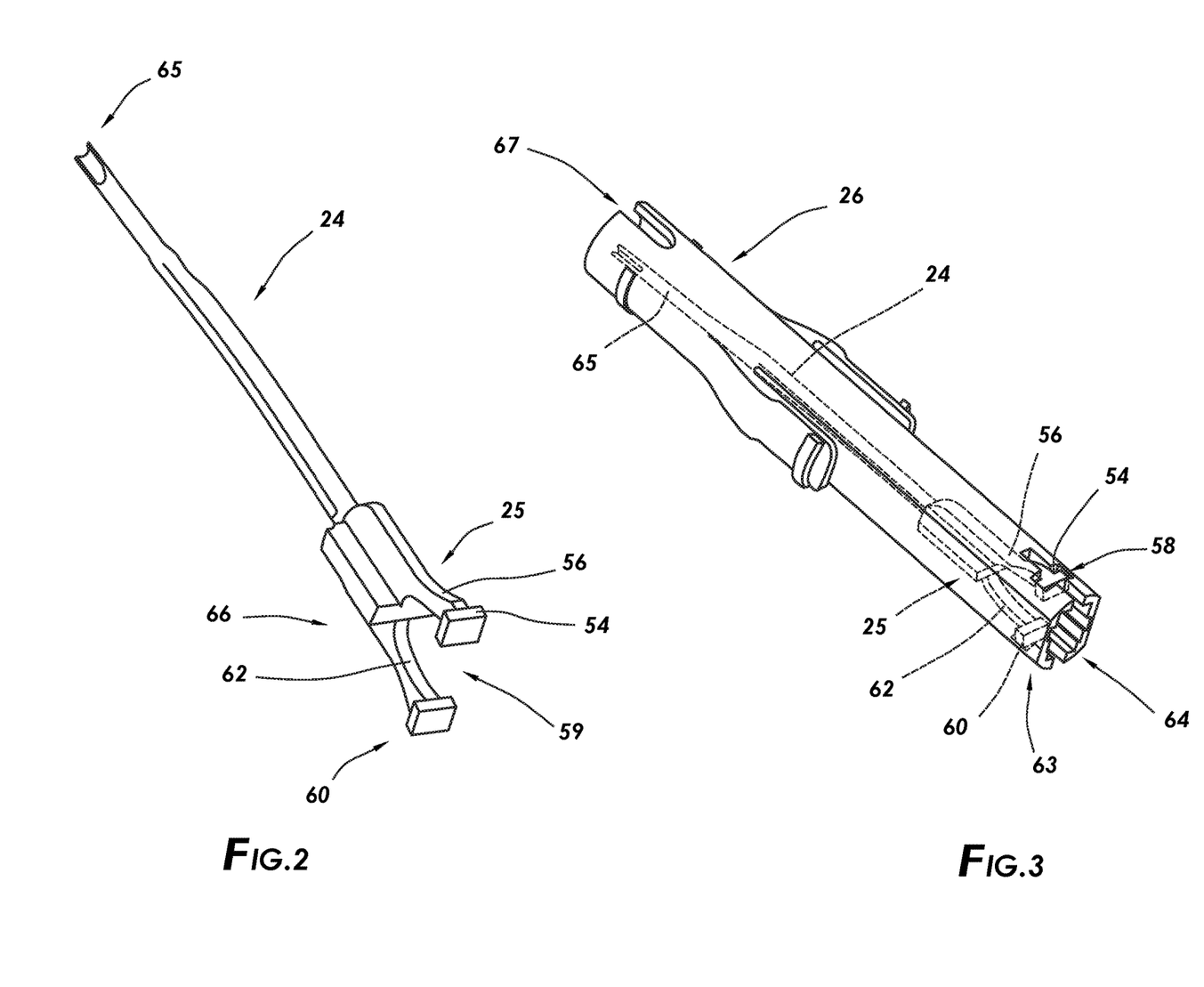
FIG. 2 illustrates a top perspective view of a plunger, in accordance with some embodiments of the present disclosure.
FIG. 3 illustrates side view of a plunger disposed within a plunger case, in accordance with some embodiments of the present disclosure.

FIG. 2 illustrates a top perspective view of the plunger 24 in accordance with particular embodiments of the present disclosure. The plunger 24 may be an elongated member with a plunger tip 65 positioned at a distal end of the plunger 24. The tail 25 may be positioned on a proximal end 66 of the plunger 24 opposite to the plunger tip 65. The proximal end 66 may include the tail 25. The tail 25 may include a first flexible prong 56 and a second flexible prong 62. An opening 59 positioned between the first and second flexible prongs 56 and 62 may be configured to receive a portion of the push rod 20 (e.g., shown on FIG. 1). In some embodiments, a first end portion 54 and a second end portion 60 of the first and second flexible prongs 56 and 62, respectively, may be slanted, for example.

FIG. 3 illustrates a side view of the plunger 24 positioned within the plunger case 26 in an initial or locked position in accordance with some embodiments of the present disclosure. The plunger case 26 may include a first aperture 58 and a second aperture 63. The second aperture 63 may be positioned opposite to the first aperture 58. As illustrated, the plunger 24 may be positioned in the plunger case 26. The first end portion 54 of the first flexible prong 56 of the plunger 24 may protrude through the first aperture 58 of the plunger case 26. The second end portion 60 of the second flexible prong 62 may protrude through the second aperture 63 of the plunger case 26. With the first flexible prong 62 and the second flexible prong 64 received in the first aperture 58 and the second aperture 63, respectively, the plunger 24 may be locked in a locked position within the plunger case 26 with restricted axial movement. The plunger case 26 may include a proximal end opening 64 adjacent to the tail 25 of the plunger 24, and a distal end opening 67 adjacent to the plunger tip 65. The proximal end opening 64 allows the push rod 20 (e.g., shown on FIG. 1) to contact the plunger 24. As previously described, the push rod 20 may be received within the opening 59 between the first flexible prong 56 and the second flexible prong 62. The first and second flexible prongs 56 and 62 may be configured to flex inward due to the interaction with one or more features on the internal portion of the housing 22 of the handpiece 10 as the plunger case 26 is received into the housing 22. As the first and second flexible prongs 56 and 62 move inward, the plunger 24 is released from the locked position within the plunger case 26. As the first flexible prong 56 and the second flexible prong 62 are flexed inward, the first and second flexible prongs 56 and 62 may contact and lock the push rod 20 as the push rod 20 is received within the opening 59. The push rod 20 may then drive the plunger 24 through the plunger case 26 such that the plunger tip 65 moves through the distal end opening 67.

Figures 4, 5:
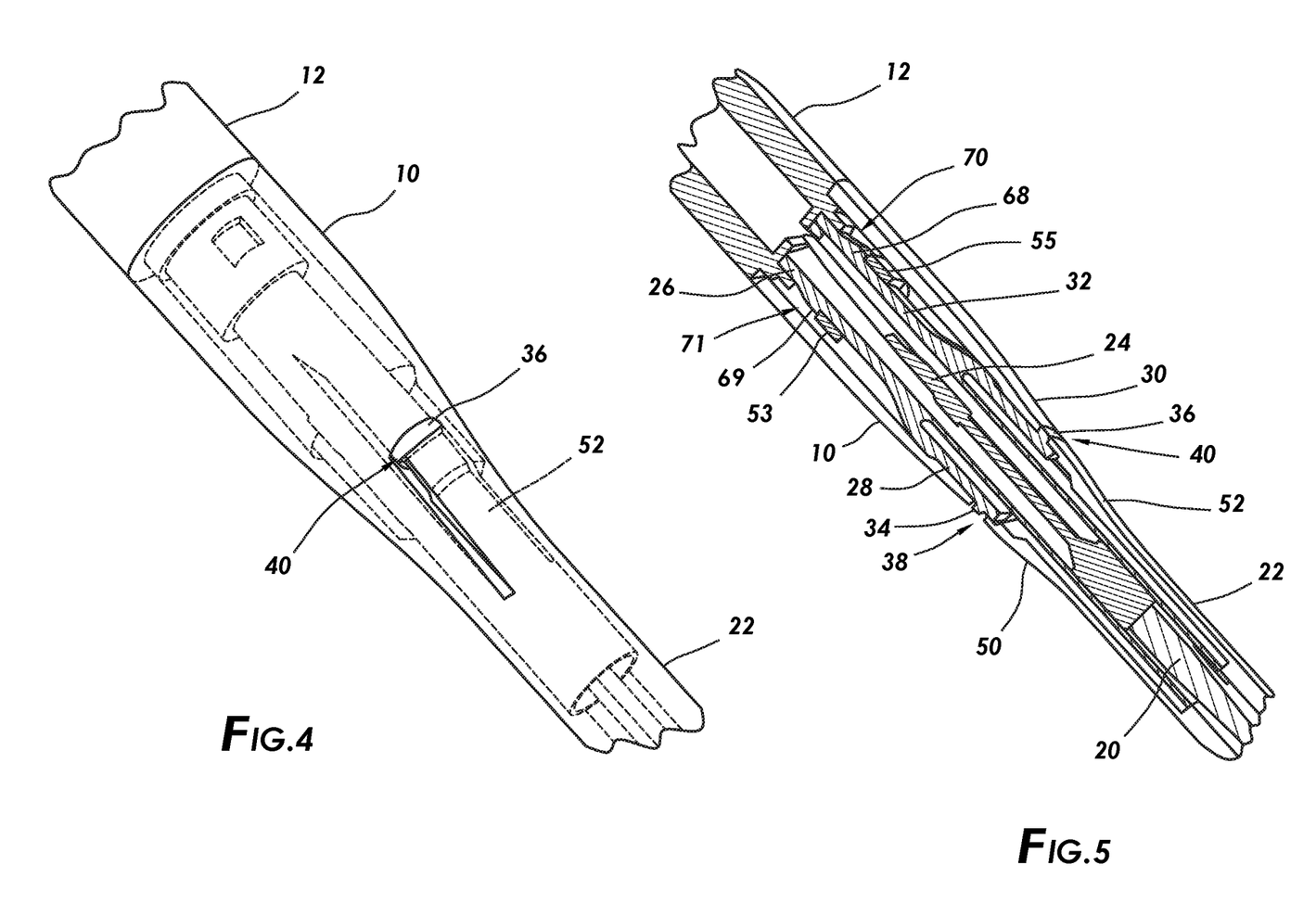
FIG. 4 illustrates a cutaway view of a plunger case of an IOL cartridge removably attached to a handpiece, in accordance with some embodiments of the present disclosure.
FIG. 5 illustrates a side cross-sectional view of an IOL cartridge locked to a handpiece, in accordance with some embodiments of the present disclosure.

FIG. 4 illustrates the IOL cartridge 12 locked to the handpiece 10 in accordance with particular embodiments of the present disclosure. As shown in FIG. 4, a portion of the handpiece 10 may be positioned over and around a portion of the IOL cartridge 12 that may include the plunger case 26. As discussed with respect to FIG. 1, the handpiece 10 may include the housing 22, flexible clip 52 formed as part of the housing 22, and the slot 40 disposed in the housing 22. The slot 40 may be adjacent to flexible clip 52. As illustrated, the IOL cartridge 12 may be positioned at least partially in the housing 22 of the handpiece 10, whereby tab 36 of the IOL cartridge 12 extends into the slot 40, thereby locking the IOL cartridge 12 to the handpiece 10. The tab 36 of the IOL cartridge 12 abuts the clip 52. Although not shown, on an opposite side of the handpiece 10, the tab 34 of the IOL cartridge 12 may also lock into the slot 38 on the housing 22 similarly to how the tab 36 locks into the slot 40.

FIG. 5 illustrates a cross-section of a portion of the IOL cartridge 12 locked to a portion of the handpiece 10, in accordance with particular embodiments of the present disclosure. As illustrated, the IOL cartridge 12 is at least partially disposed in the handpiece 10. The IOL cartridge 12 may include the plunger 24 and the plunger case 26. The IOL cartridge 12 may be positioned in the handpiece 10 with the tabs 34 and 36 of the plunger case 26 extending into the slots 38 and 40 of the housing 22 to lock the IOL cartridge 12 to the handpiece 10. The tabs 34 and 36 may be formed on end portions of the flexible members 28 and 30 and may abut the flexible clips 50 and 52 of the handpiece 10. In particular embodiments, the plunger case 26 may be attached to the handpiece 10 via protrusions 68 and 69 of the plunger case 26 that may extend into internal slots 70 and 71 adjacent to first and second internal latches 53 and 55 of the handpiece 10. As illustrated, the push rod 20 of the handpiece 10 may be removably attached to the plunger 24.

Figure 6:
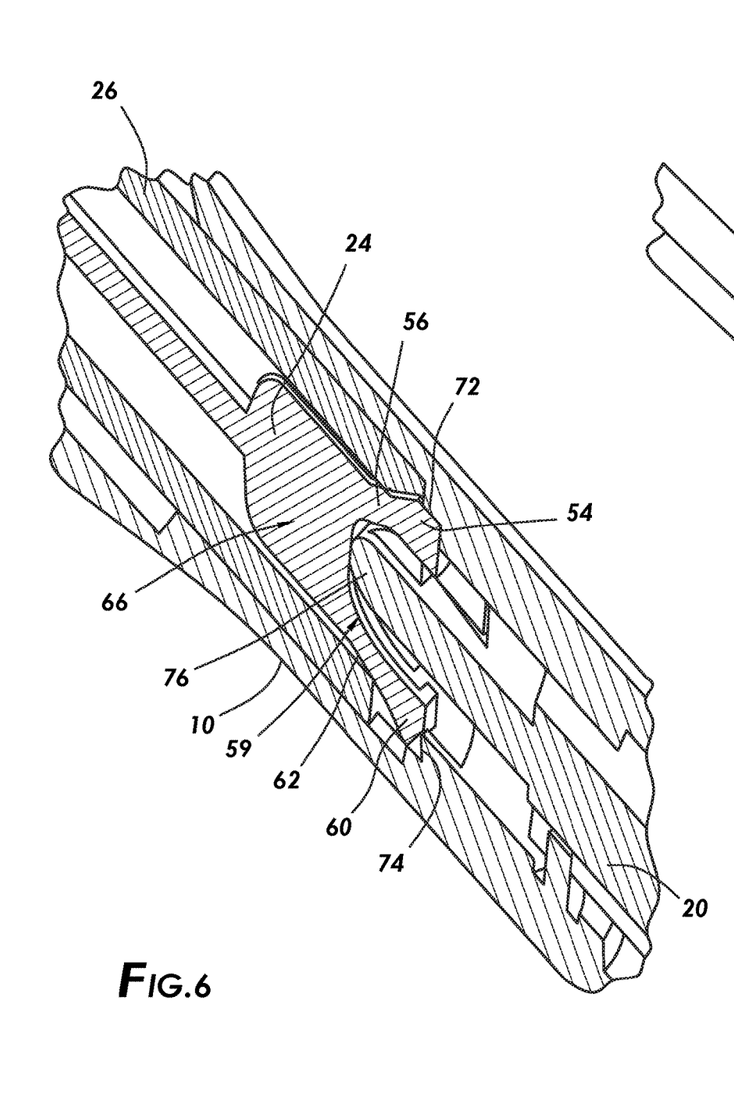
FIG. 6 illustrates a side cross-sectional view of a plunger case disposed within a handpiece, in accordance with some embodiments of the present disclosure.

FIG. 6 illustrates a cross-sectional view taken at a plane different from that of the cross-sectional view of FIG. 5 of another, more proximal portion of the plunger case 26 disposed within a more proximal portion of the handpiece 10 in accordance with particular embodiments of the present disclosure. The plunger case 26 may contain the plunger 24 with the first flexible prong 56 and the second flexible prong 62. As illustrated, the first end portion 54 of the first flexible prong 56 and the second end portion 60 of the second flexible prong 62 may extend to contact first and second internal projections 72 and 74 of the handpiece 10. The first and second internal projections 72 and 74 may contact the first and second end portions 54 and 60 and squeeze or move the first and second flexible prongs 56 and 62 inward during installation of the plunger case 26 into the handpiece 10. The inward movement of the first and second flexible prongs 56 and 62 may unlock or release the plunger 24 from a locked position (e.g., locked for shipping and/or storage, as previously noted) by releasing portions of the first and second flexible prongs 56 and 62 from the first aperture 58 and the second aperture 63, respectively, of the plunger case 26, as previously discussed with respect to FIG. 3. As the first and second flexible prongs 56 and 62 are pushed inward by the first and second internal projections 72 and 74 of the handpiece 10, a distal end 76 of the push rod 20 is received in the opening 59 at the proximal end 66 of the plunger 24 and locked in place between the first and second flexible prongs 56 and 62 of the plunger 24 that have been displaced or depressed inward.

Figure 7:
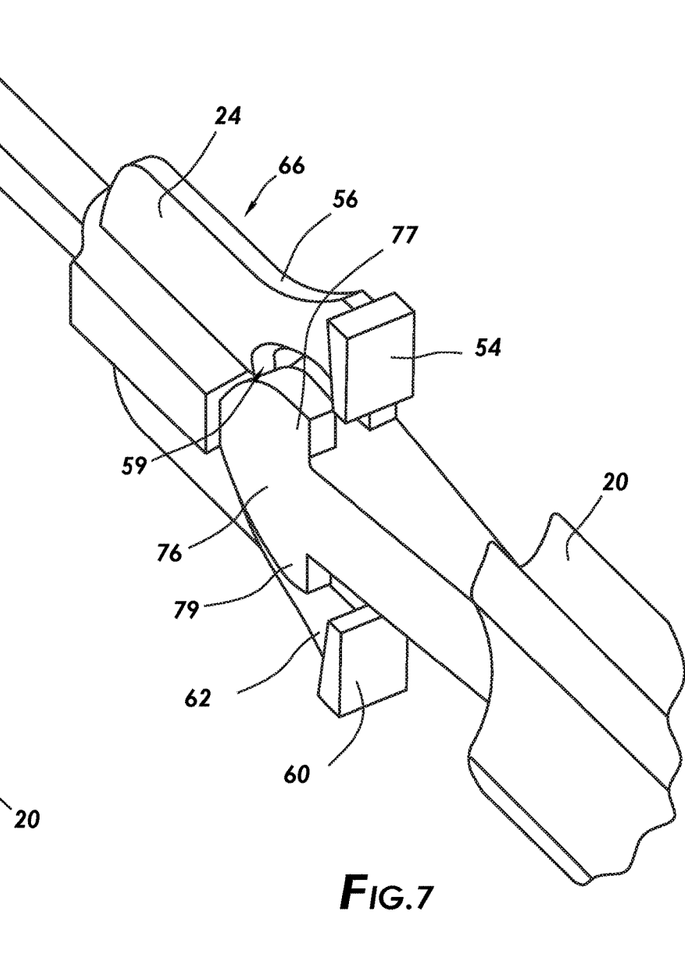
FIG. 7 illustrates a side perspective view of a plunger receiving a push rod, in accordance with some embodiments of the present disclosure.

FIG. 7 provides a further illustration of the interaction between the distal end 76 of the push rod 20 and the proximal end 66 of the plunger 24 depicted in FIG. 6. For example, FIG. 7 illustrates the push rod 20 secured to the plunger 24 in accordance with particular embodiments of the present disclosure. As further illustrated in FIG. 7, the opening 59 at the proximal end 66 of the plunger 24 is positioned between the first flexible prong 56 and the second flexible prong 62 of the plunger 24. The distal end 76 of the push rod 20 may be received within the opening 59 of the plunger 24 between the first and second flexible prongs 56 and 62. In some embodiments, the distal end 76 of the push rod 20 may include a first side protrusion 77 and a second side protrusion 79, which may be sized to fit within the opening 59 of the proximal end 66 of the plunger 24, between the first flexible prong 56 and the second flexible prong 62. As the distal end 76, including the first side protrusion 77 and the second side protrusion 79, of the push rod 20 is inserted into the opening 59 of the plunger 24, the first and second side protrusions 77 and 79 may push against and past the first end portion 54 of the first flexible prong 56 and the second end portion 60 of the second flexible prong 62, respectively. Thus, the first and second side protrusions 77 and 79 of the push rod 20 may be disposed distal to the first end portion 54 of the first flexible prong 56 and the second end portion 60 of the second flexible prong 62, respectively. The first and second flexible prongs 56 and 62, including the first end portion 54 and the second end portion 60, respectively, of the plunger 24 may then be clamped inward upon the distal end 76 of the push rod 20, with the first and second end portions 54 and 60 positioned proximal to the first and second side protrusions 77 and 79 of the distal end 76 of the push rod 20. Thus, the distal end 76 of the push rod 20 may be secured within the opening 59 of the plunger 24, thereby locking the push rod 20 to the plunger 24.

Figure 8:
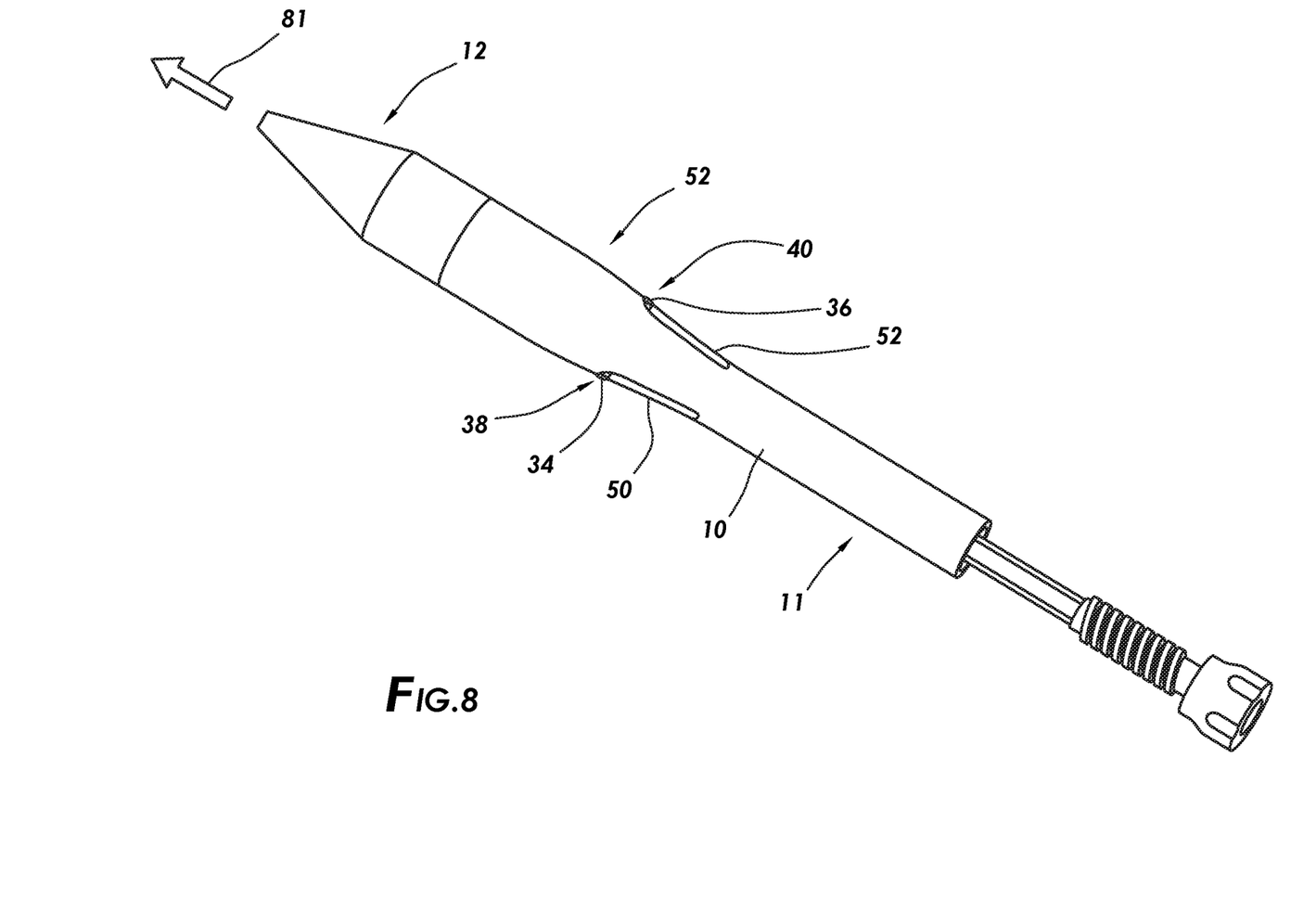
FIG. 8 illustrates a top perspective view of an insertion tool, in accordance with some embodiments of the present disclosure.

FIG. 8 illustrates the handpiece 10 removably attached to the IOL cartridge 12 to form the IOL insertion tool 11, in accordance with particular embodiments of the present disclosure. The IOL cartridge 12 may at least partially disposed in the handpiece 10. The IOL cartridge 12 may be positioned with the tabs 34 and 36 of the plunger case 26 (e.g., shown on FIG. 5) extending into the slots 38 and 40 of the handpiece 10. As shown, the tabs 34 and 36 extend into the slots 38 and 40, respectively, and abut the flexible clips 50 and 52, respectively, of the handpiece 10. To remove the IOL cartridge 12 from the handpiece 10, the flexible clips 50 and 52 may be depressed and held, while simultaneously pulling the IOL cartridge 12 away from and out of the handpiece 10, for example. By depressing the flexible clips 50 and 52, the tabs 34 and 36 of the flexible members 28 and 30, respectively, may be pushed inward and removed or released from the slots 38 and 40 of the housing 22 of the handpiece 10. The plunger case 26, including the flexible members 28 and 30 may then be free to slide in a distal direction, according to arrow 81, through the inside of the housing 22 and ultimately out of the distal end of the handpiece 10.

With reference to FIGS. 1-8, an exemplary technique for assembling an insertion tool, such as IOL insertion tool 11, in accordance with particular embodiments of the present disclosure is described as follows. First, the plunger case 26 of the IOL cartridge 12 may be inserted into the handpiece 10. As the plunger case 26 is inserted into the handpiece 10, the distal end 76 of the pushrod 20 may be received into the opening 59 of the proximal end 66 of the plunger 24 (e.g., best shown on FIG. 6). As the housing 22 of the handpiece 10 passes over the plunger case 26 during insertion of the IOL cartridge 12 into the handpiece 10, the first internal projection 72 and the second internal projection 74 of the inside of the housing 22 of the handpiece 10 pass along the first end portion 54 of the first flexible prong 56 and the second end portion 60 of the second flexible prong 62, respectively, which causes the first and second flexible prongs 56 and 60 to be pushed inward. The first and second end portions 54 and 60 are then positioned around the first and second side protrusions 77 and 79 of the push rod 20, respectively, to secure the distal end 76 of the push rod 20 between the flexible prongs 56 and 62 of the plunger 24 (e.g., best shown on FIGS. 6 and 7). At this point, the plunger 24 has been unlocked from the plunger case 26. As the housing 22 of the handpiece 10 is moved to its final position around the plunger case 26, the tabs 34 and 36 of the flexible members 28 and 30, respectively, of the plunger case 26 may then extend into the slots 38 and 40 of the handpiece 10, respectively, as best seen in FIG. 5, thus locking the external housing 22 of the handpiece 10 to the plunger case 26 and completing assembly of the IOL insertion tool 11. The push rod 20 of the handpiece 10 may then be actuated or advanced forward in a distal direction to drive the plunger 24 axially forward through the plunger case 26 and compartment 15 of the IOL cartridge 12 to move the IOL 14 from the IOL cartridge 12 into an eye.

To disassemble the assembled IOL insertion tool 11 (e.g., as best shown on FIG. 8), the flexible clips 50 and 52 may be depressed and held, thereby unlocking the plunger case 26 from the handpiece 10. Next, the IOL cartridge 12 may be pulled away from the handpiece 10 thereby sliding the plunger case 26 out from the handpiece 10 to thus separate the IOL cartridge 12 and the separate handpiece 10 from one another (e.g., as best shown on FIG. 1).

Figure 9:
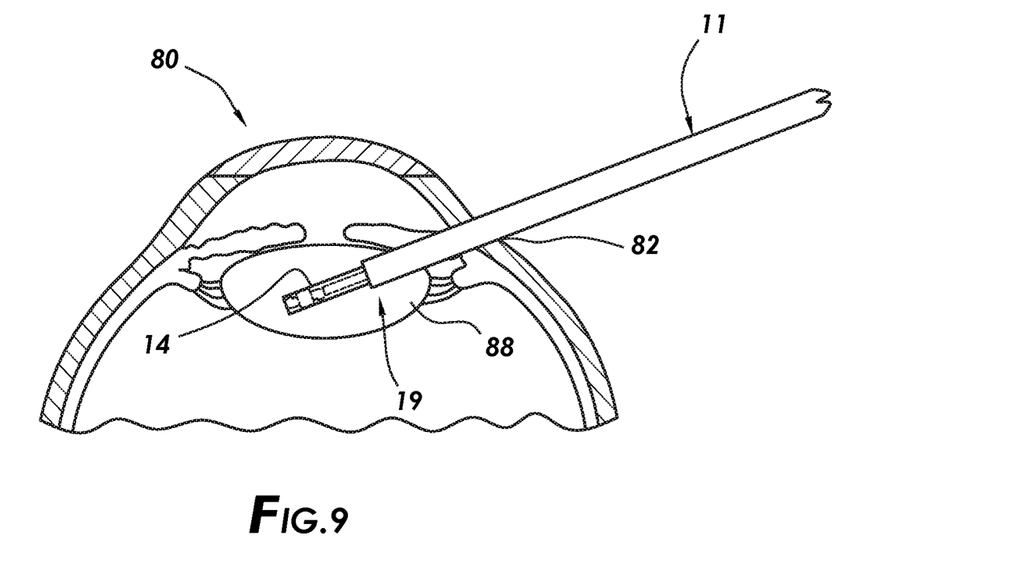
FIGS. 9 and 10 illustrate implantation of an IOL in accordance with some embodiments of the present disclosure.
Figure 10:
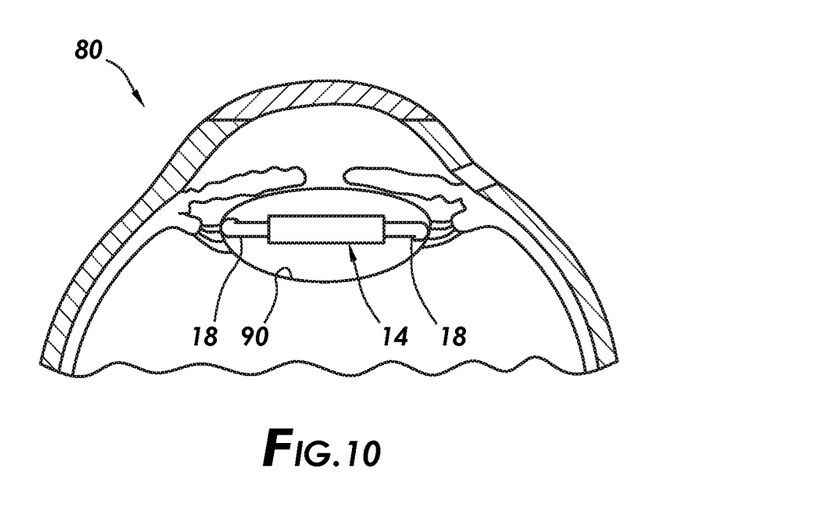

An exemplary technique for implantation of an IOL, such as IOL 14, into an eye 80 of a patient will now be described with respect to FIGS. 9 and 10. An incision 82 may be made in the eye 80 by a surgeon. For example, the incision 82 may be made through the sclera of the eye 80. The incision 82 may be a suitable width or length. After the incision 82 is made, the nozzle 19 of the IOL insertion tool 11 may be inserted through the incision 82 into an interior portion 88 of the eye 80. The IOL insertion tool 11 may be actuated to dispense the IOL 14 into a capsular bag 90 of the eye 80.

In some embodiments, the IOL 14 may be delivered in a folded (or rolled configuration) and allowed to unfurl after ejection from the IOL insertion tool 11. Upon dispensation, the IOL 14 should unfurl and settle within the capsular bag 90 of the eye 80, as shown on FIG. 10. The haptic extensions 18 may be manipulated, for example, to engage an equator of the capsular bag 90. The haptic extensions 18 may engage the capsular bag 90 to secure the IOL 14 in the capsular bag 90.

Use of the methods and systems described herein may provide numerous benefits and advantages over other IOL delivery systems. For example, as previously noted, particular embodiments allow interchangeable utilization between different drive mechanisms and various preloaded IOL cartridge designs. This interchangeability offers a simplified and uniform process for pairing drive mechanisms to preloaded IOL cartridges. Thus, a variety of handpieces employing different types of drive mechanisms may be used with each of numerous different types of IOL cartridges, and therefore different types of IOLs. For example, a user may readily select between multiple types of drive mechanisms he or she wishes to use depending on the type of IOL and/or the type of IOL cartridge. Additionally, while one user may prefer to use a first type of drive mechanism handpiece for a given IOL cartridge, a different user may have the option of using a second type of drive mechanism handpiece for the same given type of IOL cartridge. Importantly, by allowing for a common, or standard, interface for securing the handpieces to the IOL cartridges, the user experience of securing a handpiece to an IOL cartridge may be substantially the same, regardless of the type of drive mechanism or type of IOL cartridge, and thus IOL, being used, which may also increase ease-of-use for an operator as well as streamline IOL delivery procedures.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for delivery of an intraocular lens (IOL), comprising:
   an IOL cartridge, comprising:
      a nozzle;
      a compartment for receiving the IOL, the nozzle in fluid communication with the compartment;
      a plunger case in fluid communication with the compartment, the plunger case comprising at least one flexible member extending from an outer surface of the plunger case; and a plunger disposed within the plunger case, wherein the plunger case is configured to removably attach to a handpiece; and the handpiece, comprising:

a housing; and a push rod disposed within the housing, the push rod comprising a distal end configured to removably attach to the plunger, wherein:

the plunger comprises a tail comprising a plurality of flexible prongs that extend to form an opening configured to receive the distal end of the push rod, portions of the flexible prongs extend through apertures of the plunger case, and the housing comprises internal projections configured to contact the portions of the flexible prongs and move the flexible prongs inward to lock the distal end of the push rod within the opening of the plunger.

2. The apparatus of claim 1, wherein the housing of the handpiece comprises at least one flexible clip configured to engage with the at least one flexible member of the plunger case.

3. The apparatus of claim 1, wherein the portions of the flexible prongs are slanted.

4. The apparatus of claim 3, wherein the flexible prongs are configured to clamp and secure the push rod.

5. The apparatus of claim 1, wherein the compartment comprises the IOL.

6. An apparatus for delivery of an intraocular lens (IOL), comprising:

a handpiece, comprising:

a housing comprising flexible clips; and a push rod disposed within the housing, wherein a distal end of the push rod is configured to removably attach to an IOL cartridge; and the IOL cartridge, comprising:

a compartment for receiving the IOL;

a plunger case in fluid communication with the compartment, wherein the plunger case is configured to removably attach to the handpiece; and a plunger disposed within the plunger case, wherein:

the plunger comprises a tail comprising a plurality of flexible prongs that extend to form an opening configured to receive the distal end of the push rod, portions of the flexible prongs extend through apertures of the plunger case, and the housing of the handpiece comprises internal projections configured to move the flexible prongs inward to lock the distal end of the push rod within the opening of the plunger.

7. The apparatus of claim 6, wherein portions of the flexible prongs are slanted.

8. The apparatus of claim 7, wherein the flexible prongs are configured to clamp and secure the push rod.

9. A method for delivery of an intraocular lens (IOL) into an eye, comprising:

inserting a plunger case of an IOL cartridge into a housing of a handpiece, the plunger case comprising at least one flexible member extending from an outer surface of the plunger case, wherein a plunger is disposed within the plunger case;

receiving a distal end of a push rod of the handpiece between a plurality of flexible prongs of the plunger;

further inserting the plunger case within the housing of the handpiece, causing internal features of the housing to move the flexible prongs inward to release the plunger from a locked position and to secure the distal end of the push rod between the flexible prongs; and receiving at least one portion of the at least one flexible member within at least one slot of the housing of the handpiece to lock the IOL cartridge to the handpiece.

10. The method of claim 9, further comprising actuating the push rod to move the IOL from the IOL cartridge into the eye with the plunger.

11. The method of claim 10, further comprising depressing at least one flexible clip of the housing of the handpiece to depress the at least one flexible member of the plunger case in order to release the plunger case from the handpiece.

12. An apparatus for delivering an intraocular lens (IOL), comprising:

an IOL cartridge, comprising:

a compartment for receiving an IOL;

a plunger case having a distal end coupled to the compartment and a proximal end; and a plunger disposed within the plunger case, the plunger comprising a plurality of flexible prongs, the plunger case comprising flexible members extending from an outer surface of the plunger case; and a handpiece configured to be removably coupled to the plunger case and comprising:

a housing; and a push rod disposed within the housing and configured to releasably couple to the plunger of the plunger case, wherein:

the housing comprises internal projections configured to contact the flexible prongs and move the flexible prongs inward to release the plunger from a locked position and to lock a distal end of the push rod within an opening of the plunger.

* * * * *